United States Patent [19]

Fest et al.

[11] Patent Number: 4,716,176

[45] Date of Patent: Dec. 29, 1987

[54] BENZALDOXIME CARBAMATE DERIVATIVES, THEIR COMPOSITIONS AND METHOD OF USE

[75] Inventors: Christa Fest, Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 867,101

[22] Filed: May 23, 1986

[30] Foreign Application Priority Data

Jun. 12, 1985 [DE] Fed. Rep. of Germany ....... 3520943

[51] Int. Cl.⁴ .................... A01N 47/12; C07C 147/06; C07C 131/00
[52] U.S. Cl. .................................. 514/477; 558/391; 564/255
[58] Field of Search ........................ 564/255; 514/477; 558/391

[56] References Cited

U.S. PATENT DOCUMENTS 3,721,711  3/1973  Maravetz et al. .................. 564/255
4,278,613  7/1981  Sturm et al. ........................ 71/103

FOREIGN PATENT DOCUMENTS 423350  4/1967  Switzerland .

Primary Examiner—Donald D. Moyer
Assistant Examiner—L. Hendriksen
Attorney, Agent, or Firm—Sprung Horn Kramer & Woods

[57] ABSTRACT

Novel fungicidally active benzaldoxime carbamates of the formula

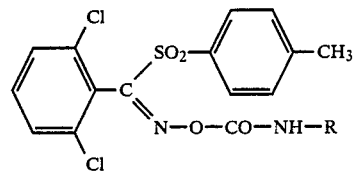

in which
R is alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl which has 5 to 7 carbon atoms and is optionally substituted by alkyl having 1 to 4 carbon atoms, or phenyl which is optionally substituted by substituents independently selected from the group consisting of alkyl having 1 to 6 carbon atoms, alkoxy having 1 to 4 carbon atoms, halogen, and halogenoalkoxy and halogenoalkyl each having 1 to 4 carbon atoms and 1 to 5 halogen atoms.

14 Claims, No Drawings

BENZALDOXIME CARBAMATE DERIVATIVES, THEIR COMPOSITIONS AND METHOD OF USE

The present invention relates to new benzaldoxime carbamate derivatives, a process for their preparation, and their use as pest-combating agents.

A number of benzaldoximes, such as, for example, α-phenylsulphonyl-2,6-dichloro-benzaldoxime, are already known, as is their use as plant protection agents; in particular, their use in agents for combating wheat bunt (see Swiss Pat. No. 423,350) is known.

Organic sulphur compounds, such as metal salts of dithiocarbamic acids, for example zinc ethylene-1,2-bis-dithiocarbamate, are also known to be good fungicides (see, for example, R. Wegler, "Chemie der Pflanzenschutzund Schadlingsbekámpfungsmittel" [Chemistry of Plant Protection Agents and Pest-combating Agents], Volume 2, page 65, Springer-Verlag, Berlin-Heidelberg-New York, 1970).

However, their action is not always completely satisfactory under certain conditions, for example at low application rates.

New benzaldoxime carbamate derivatives of the formula (I)

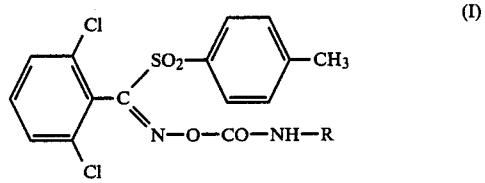

in which

R represents alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl which has 5 to 7 carbon atoms and is optionally monosubstituted to pentasubstituted by alkyl having 1 to 4 carbon atoms, or phenyl which is optionally monosubstituted to pentasubstituted by identical or different substituents from amongst alkyl having 1 to 6 carbon atoms, alkoxy having 1 to 4 carbon atoms, halogenoalkoxy or halogenoalkyl having 1 to 4 carbon atoms and 1 to 5 halogen atoms and halogen, have been found.

It has also been found that the benzaldoxime carbamate derivatives of the formula (I)

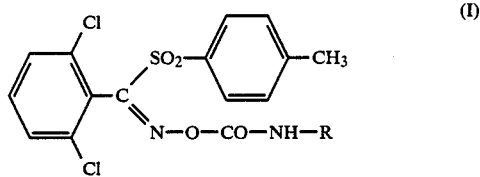

in which

R represents alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl which has 5 to 7 carbon atoms and is optionally monosubstituted to pentasubstituted by alkyl having 1 to 4 carbon atoms, or phenyl which is optionally monosubstituted to pentasubstituted by identical or different substituents from amongst alkyl having 1 to 6 carbon atoms, alkoxy having 1 to 4 carbon atoms, halogenoalkoxy or halogenoalkyl having 1 to 4 carbon atoms and 1 to 5 halogen atoms and halogen, are obtained when α-(4-methyl-phenylsulphonyl)-2,6-dichlorobenzaldoxime of the formula (II)

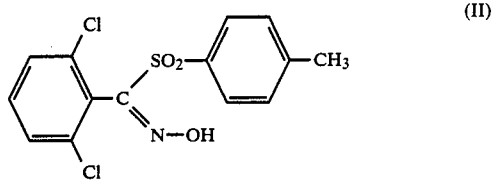

is reacted with isocyanates of the formula (III) in which R has the meaning given above, if appropriate in the presence of solvents or diluents at temperatures from 0° C. to 100° C.

The benzaldoxime carbamate derivatives according to the invention, of the formula (I), possess powerful biological properties, especially fungicidal properties.

Surprisingly, the compounds according to the invention exhibit substantially greater activity, in particular fungicidal activity, than the compounds known from the prior art, which are very similar compounds structurally and/or in terms of their action.

The compounds according to the invention, of the formula (I), can be obtained as syn or anti isomers, or as mixtures of these having different compositions. The invention relates both to the pure isomers and to the isomer mixtures.

Formula (I) gives a general definition of the benzaldoxime carbamate derivatives according to the invention. Preferred compounds of the formula (I) are those in which R represents straight-chain or branched alkyl having 1 to 4 carbon atoms, such as methyl, ethyl, n-propyl, iso-propyl, n-butyl, iso-butyl, sec.-butyl and tert.-butyl, halogenoalkyl having 1 to 6 carbon atoms and 1 to 3 identical or different halogen atoms, such as fluorine, chlorine, bromine and iodine, for example 2-chloroethyl, 3-chloro-n-propyl, 4-chloro-n-butyl, 4-chloro-n-pentyl and 6-chloro-n-hexyl, or cyanoalkyl having 1 to 5 carbon atoms in the alkyl part, for example 3- or 5-cyano-n-pentyl, or represents tosyl or benzyl, or represents cycloalkyl which has 6 or 7 carbon atoms and is optionally monosubstituted to trisubstituted by identical or different substituents from amongst alkyl having 1 to 3 carbon atoms, such as methyl, ethyl, n-propyl and iso-propyl, or represents phenyl which is optionally monosubstituted to trisubstituted by identical or different substituents from amongst alkyl having 1 to 4 carbon atoms, such as, for example, methyl, ethyl, n-propyl, iso-propyl, n-butyl, iso-butyl, sec.-butyl and tert.-butyl, alkoxy having 1 to 3 carbon atoms, suoh as methoxy, ethoxy, n-propoxy and iso-propoxy, halogenoalkyl or halogenoalkoxy having 1 to 3 carbon atoms and 1 to 3 halogen atoms, such as fluorine, chlorine, bromine and iodine, such as, for example, trifluoromethyl, trichloromethyl, dichlorofluoromethyl, 2-chloroethyl, 2-fluoroethyl, trifluoromethoxy, dichlorofluoromethoxy, 2-chloroethoxy and 2-fluoroethoxy, and halogen, such as fluorine, chlorine, bromine and iodine.

Particularly preferred compounds of the formula (I) are those in which

R represents methyl, ethyl, n-propyl, iso-propyl, n-butyl, iso-butyl, tert.-butyl, 6-chloro-n-hexyl, 5-cyanon-pentyl, tosyl, benzyl, cyclohexyl or cyclohexyl which is monosubstituted to trisubstituted by methyl or ethyl.- phenyl or phenyl which is monosubstituted to trisubstituted by identical or different substituents from amongst methyl, ethyl, n-propyl, iso-propyl, methoxy, ethoxy, trifluoromethoxy, trifluoromethyl, chlorine and fluorine.

Compounds of the formula (I) in which

R represents methyl, ethyl, n-propyl, iso-propyl, n-butyl, iso-butyl, tert.-butyl, 6-chloro-n-hexyl, 5-cyano-n-pentyl, benzyl, tosyl, cyclohexyl, 3,5,5-trimethylcyclohexyl, 4-methyl-cyclohexyl, phenyl, 4-trifluoromethoxy-phenyl, 2-, 3- or 4-methyl-phenyl, 3-chloro-4-methyl-phenyl, 3-methyl-4-chlorophenyl, 3- or 4-chlorophenyl, 2,6-, 3,4- or 3,5-dichloro-phenyl, 3-trifluoromethyl-phenyl, 4-ethoxy-phenyl, 3-chloro-4-trifluoromethylphenyl or 3,6-di-isopropyl-phenyl, may be mentioned in particular.

Very particularly the compounds of the formula (I) in which

R represents methyl, ethyl, tosyl, 4-trifluoromethoxyphenyl or 3,5,5-trimethyl-cyclohexyl.

If α-(4-methyl-phenylsulphonyl)-2,6-dichlorobenzaldoxime and methyl isocyanate are used as starting materials, the course of the reaction of the process according to the invention can be represented by the following equation:

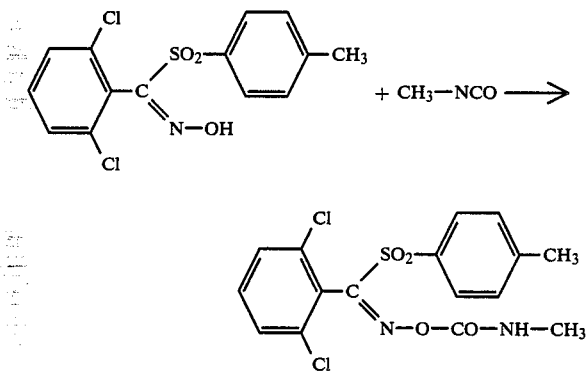

Formula (II) gives a definition of the α-(4-methylphenylsulphonyl)-2,6-benzaldoxime required as a starting material for carrying out the process according to the invention. This compound and its preparation are known (see, for example, Chem. Abstracts 83:27759e=-Tetrahedron 1975, 31(6), pages 597–600).

Formula (III) gives a general definition of the isocyanates furthermore required as starting materials. These are known compounds of organic chemistry.

The process according to the invention can, if appropriate, be carried out in the presence of a solvent or diluent. Suitable solvents or diluents are in principle all inert organic solvents. Hydrocarbons, optionally chlorinated, such as, for example, benzene, toluene, xylene, methylene chloride, chloroform, carbon tetrachloride, chlorobenzene and dichlorobenzene, are preferably used.

The reaction temperatures can be varied within a relatively wide range. In general, the reaction is carried out at between 0° and 100° C., preferably between 15° and 50° C.

In carrying out the process according to the invention, the reactants are allowed to react with one another in approximately equimolar ratios. Since the reaction is occasionally exothermic, it is advisable to cool. Working up of the reaction mixture is carried out in a conventional manner, mainly by filtration under suction, washing and drying of the precipitated reaction product.

To complete the reaction, a few drops of a base, such as, for example, triethylamine, can, if required, be added.

The active compounds according to the invention exhibit a powerful microbicidal action and can be employed in practice for combating undesired microorganisms. The active compounds are suitable for use as plant protection agents, especially as fungicides.

Fungicidal agents in plant protection are employed for combating plasmodiophoromycetes, Oomycetes, Chytridiomycetes, Zygomycetes, Ascomycetes, Basidiomycetes and Deuteromycetes.

Some causative organisms of fungal and bacterial diseases included under the abovementioned main headings are mentioned below as non-limiting examples: Pythium species, such as, for example, *Pythium ultimum*; Phytophthora species, such as for example, *Phytophthora infestans*: Pseudoperonospora species, such as, for example, *Pseudoperonospora humuli* or *Pseudoperonospora cubense*; Plasmopara species, such as, for example, *Plasmopara viticola*; Peronospora species, such as, for example, *Peronospora pisi-* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea*(- Conidial form: Drechslera, synonym: Helminthosporium); Cochliobolus species, such as, for example, *Cochliobolus sativus*(Conidial form: Drechslera, synonym: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda or Ustilago, avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae*; Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be used with particularly good success for combating vegetable diseases caused by, for example, Phytophthora infestans, for combating rice diseases caused by, for example, Pyricularia oryzae, and for combating cereal diseases cause by, for example, Leptosphaeria nodorum or Pyrenophora teres.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants such as halogenated hydrocarbons as well as butane, propane, nitrogen and carbon dioxide. As solid carriers there are suitable: for example ground natural minerals, such as kaolins, clays, talc, chalk, quartz, attapulgite, monmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Other additives can be mineral or vegetable oils.

It is possible to use colorants such as inorganic pigments, for example iron oxide, titanium oxide and Prussian Blue and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and as mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, scattering, dusting, foaming, brushing on, etc. It is also possible to apply the active compounds by the ultra low volume method or to inject the active compound preparation or the active compound itself into the soil. It is also possible to treat the seed of the plants.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

Preparation examples

EXAMPLE 1

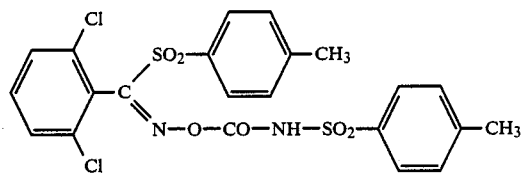

36 g. (0.1 mole) of α-(4-methyl-phenyl-sulphonyl)-2,6-dichlorobenzaldoxime are dissolved in 200 ml of methylene chloride, and 19.7 g. (0.1 mole) of 4-methylphenylsulphonyl isocyanate are added, a few drops of triethylamine being introduced in order to complete the reaction. The reaction is exothermic. The mixture is stirred overnight at room temperature. The reaction product is precipitated, and is filtered off under suction, washed and dried. 23 g. (41% of theory) of the desired substance having a melting point of 157° C. are obtained.

The following compounds of the formula (I)

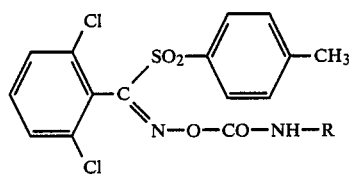

are prepared in a manner analogous to Example 1 and 31 (hereinbelow):

| Example No. | R | Physical data (melting point °C.) |
|---|---|---|
| 2 | —C₂H₅ | 182 |
| 3 | —CH₃ | 179 |
| 4 | 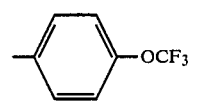 | 176 |

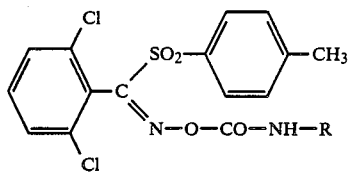

(I)

are prepared in a manner analogous to
Example 1 and 31 (hereinbelow):

| Example No. | R | Physical data (melting point °C.) |
|---|---|---|
| 5 | 3,3,5-trimethylcyclohexyl (CH₃, H, CH₃, CH₃) | 173 |
| 6 | —C₃H₇—iso | 187 |
| 7 | —C₃H₇—n | 184 |
| 8 | —C₄H₉—n | 177 |
| 9 | —(CH₂)₆—Cl | 109 |
| 10 | —C₄H₉—iso | 192 |
| 11 | —(CH₂)₅—CN | 168 |
| 12 | 4-methylcyclohexyl (H, CH₃) | 171 |
| 13 | —CH₂—C₆H₅ | 207 |
| 14 | 2-methylphenyl (CH₃) | 190 |
| 15 | 3-methylphenyl (CH₃) | 201 |
| 16 | 4-methylphenyl (CH₃) | 208 (decomposition) |
| 17 | 4-chloro-3-methylphenyl (Cl, CH₃) | 210 (decomposition) |
| 18 | 3-chloro-2-methylphenyl (CH₃, Cl) | 202 (decomposition) |

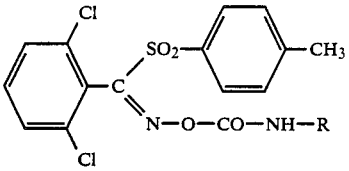

(I)

are prepared in a manner analogous to
Example 1 and 31 (hereinbelow):

| Example No. | R | Physical data (melting point °C.) |
|---|---|---|
| 19 | 3-chlorophenyl (Cl) | 198 (decomposition) |
| 20 | 3,4-dichlorophenyl (Cl, Cl) | 194 (decomposition) |
| 21 | 3,5-dichlorophenyl (Cl, Cl) | 193 (decomposition) |
| 22 | 3-trifluoromethylphenyl (CF₃) | 193 (decomposition) |
| 23 | 4-ethoxyphenyl (OC₂H₅) | 192 (decomposition) |
| 24 | 2,6-diisopropylphenyl (C₃H₇—iso, C₃H₇—iso) | 190 |
| 25 | —C₄H₉—tert. | 174 |
| 26 | 4-chloro-3-trifluoromethylphenyl (Cl, CF₃) | 186 |
| 27 | 4-chlorophenyl (Cl) | 206 |
| 28 | cyclohexyl (H) | 172 |

-continued

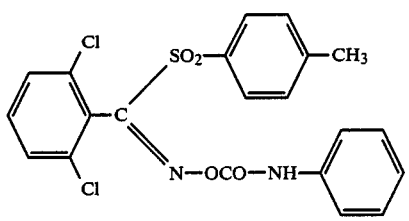

are prepared in a manner analogous to Example 1 and 31 (hereinbelow):

| Example No. | R | Physical data (melting point °C.) |
| --- | --- | --- |
| 29 | Cl-[ring]-Cl | 191 |
| 30 | —C$_4$H$_9$—iso | 192 |

EXAMPLE 31

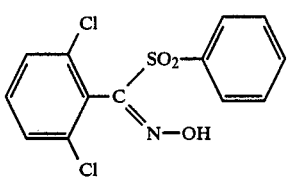

25.5 g (0.075 mole) of α-(4-methyl-phenyl-sulphonyl)-2,6-dichlorobenzaldoxime are dissolved in 200 ml of methylene chloride, and 8.9 g (0.075 mole) of phenyl isocyanate are added, a few drops of triethylamine being introduced in order to complete the reaction. The reaction is exothermic. The mixture is stirred overnight at room temperature. The reaction product is precipitated with acetone. 18 g (29% of theory) of the desired substance having a melting point of 198° C. are obtained.

USE EXAMPLES

In the use examples below, the compounds listed below are used as comparative substances

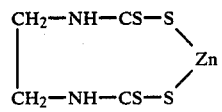
(A)

α-Phenylsulphonyl-2,6-dichlorobenzaldoxime and

```
CH2—NH—CS—S
              \
               Zn                 (B)
              /
CH2—NH—CS—S
``` zinc ethylene-1,2-bis-dithiocarbamate

Example A

Phytophthora test (tomato)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to preparation Examples 1, 2, 3 and 4.

EXAMPLE B

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation Examples 1, 2 and 3.

EXAMPLE C

Leptosphaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compound according to preparation Example 1.

It will be understood that the specification and examples are illustrative but not limitative of the present invention and that other embodiments within the spirit and scope of the invention will suggest themselves to those skilled in the art.

We claim:

1. A benzaldoxime carbamate of the formula

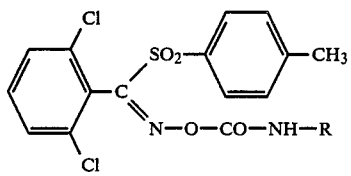

in which

R is alkyl having 1 to 6 carbon atoms, halogenoalkyl having 1 to 8 carbon atoms and 1 to 5 halogen atoms, cyanoalkyl having 1 to 6 carbon atoms in the alkyl part, tosyl, benzyl, cycloalkyl which has 5 to 7 carbon atoms and is optionally substituted by alkyl having 1 to 4 carbon atoms, or phenyl which is optionally substituted by substituents independently selected from the group consisting of alkyl having 1 to 6 carbon atoms, alkoxy having 1 to 4 carbon atoms, halogen, and halogenoalkoxy and halogenoalkyl each having 1 to 4 carbon atoms and 1 to 5 halogen atoms.

2. A carbamate according to claim 1, in which

R is alkyl having 1 to 4 carbon atoms, halogenoalkyl having 1 to 6 carbon atoms and 1 to 3 halogen atoms, cyanoalkyl having 1 to 5 carbon atoms in the alkyl part, tosyl, benzyl, cyclohexyl which is optionally monosubstituted to trisubstituted by alkyl having 1 to 3 carbon atoms, or is phenyl which is optionally substituted up to three times by substituents independently selected from the group consisting of alkyl having 1 to 4 carbon atoms, alkoxy having 1 to 3 carbon atoms, halogen, and halogenoalkyl and halogenoalkoxy each having 1 to 3 carbon atoms and 1 to 3 halogen atoms.

3. A carbamate according to claim 1, in which

R is methyl, ethyl, n-propyl, iso-propyl, n-butyl, iso-butyl, tert.-butyl, 6-chloro-n-hexyl, 5-cyano-n-pentyl, tosyl, benzyl, cyclohexyl or cyclohexyl which is monosubstituted to trisubstituted by methyl or ethyl; or phenyl or phenyl which is monosubstituted to trisubstituted by substituents independently selected from the group consisting of methyl, ethyl, n-propyl, iso-propyl, methoxy, ethoxy, trifluoromethoxy, trifluoromethyl, chlorine and fluorine.

4. A carbamate according to claim 1, in which

R is methyl, ethyl, n-propyl, iso-propyl, n-butyl, iso-butyl, tert.-butyl, 6-chloro-n-hexyl, 5-cyano-n-pentyl, benzyl, tosyl, cyclohexyl, 3,5,5-trimethylcyclohexyl, 4-methyl-cyclohexyl, phenyl, 4-trifluoromethoxy-phenyl, 2-, 3- or 4-methyl-phenyl, 3-chloro-4-methyl-phenyl, 3-methyl-4-chlorophenyl, 3- or 4-chlorophenyl, 2,6-, 3,4- or 3,5-dichlorophenyl, 3-trifluoromethylphenyl, 4-ethoxy-phenyl, 3-chloro-4-trifluoromethylphenyl or 3,6-di-isopropylphenyl.

5. A carbamate according to claim 1, in which

R is methyl, ethyl, tosyl, 4-trifluoromethoxyphenyl or 3,5,5-trimethyl-cyclohexyl.

6. A compound according to claim 1, wherein such compound is α-(4-methyl-phenyl-sulphonyl)-2,6-dichlorobenzaldoxime N-(4-methyl-phenyl-sulphonyl)-carbamate

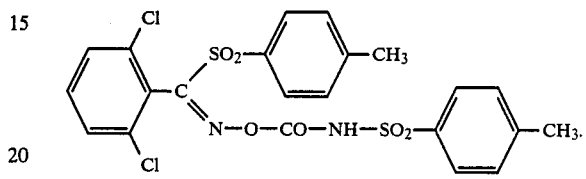

7. A compound according to claim 1, wherein such compound is α-(4-methyl-phenyl-sulphonyl)-2,6-dichlorobenzaldoxime N-ethyl-carbamate

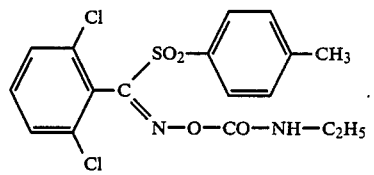

8. A compound according to claim 1, wherein such compound is α-(4-methyl-phenyl-sulphonyl)-2,6-dichlorobenzaldoxime N-methyl-carbamate

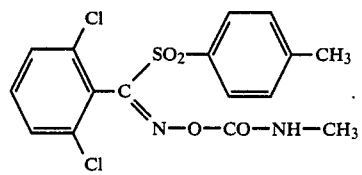

9. A compound according to claim 1, wherein such compound is α-(4-methyl-phenyl-sulphonyl)-2,6-dichlorobenzaldoxime N-(4-trifluoromethoxy-phenyl)-carbamate

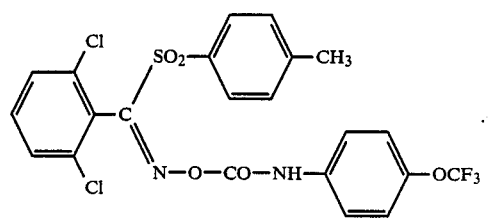

10. A compound according to claim 1, wherein such compound is α-(4-methyl-phenyl-sulphoyl)-2,6-dichlorobenzaldoxime N-(ω-cyano-n-pentyl) carbamate

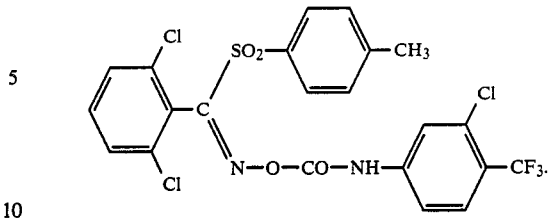

12. A fungicidal composition comprising a fungicidally effective amount of a compound according to claim 1 and a diluent.

13. A method of combating fungi which comprises applying to such fungi or to a fungus habitat a fungicidally effective amount of a compound according to claim 1.

14. A method according to claim 13 wherein such compound is
α-(4-methyl-phenyl-sulphonyl)-2,6-dichlorobenzaldoxime N-(4-methyl-phenyl-sulphonyl)-carbamate,
α-(4-methyl-phenyl-sulphonyl)-2,6-dichlorobenzaldoxime N-ethyl-carbamate,
α-(4-methyl-phenyl-sulphonyl)-2,6-dichlorobenzaldoxime N-methyl-carbamate,
α-(4-methyl-phenyl-sulphonyl)-2,6-dichlorobenzaldoxime N-(4-trifluoromethoxy-phenyl)-carbamate,
α-(4-methyl-phenyl-sulphonyl)-2,6-dichlorobenzaldoxime N-(ω-cyano-n-pentyl)-carbamate or
α-(4-methyl-phenyl-sulphonyl)-2,6-dichlorobenzaldoxime N-(3-chloro-4-trifluoromethyl-phenyl)-carbamate.

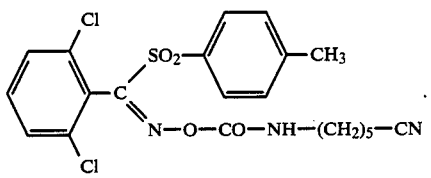

11. A compound according to claim 1, wherein such compound is α-(4-methyl-phenyl-sulphonyl)-2,6-dichlorobenzaldoxime N-(3-chloro-4-trifluoromethyl-phenyl)-carbamate

* * * * *

UNITED STATES PATENT AND TRADEMARK OFFICE
CERTIFICATE OF CORRECTION

PATENT NO. : 4,716,176

DATED : December 29, 1987

INVENTOR(S) : Christa Fest, et al.

It is certified that error appears in the above-identified patent and that said Letters Patent is hereby corrected as shown below:

| | |
|---|---|
| Col. 1, line 17 | Correct --Schädlingsbekämpfungs-mittel-- |
| Col. 2, line 56 | Delete "suoh" and substitute --such-- |
| Col. 3, line 2 | After "ethyl" delete ".⁻" and substitute --;-- |
| Col. 9, line 35 | Delete "moIe" and substitute --mole-- |
| Col. 9, line 50 | After "substances" insert --:-- |
| Col. 12, line 66 | Correct --sulphonyl-- |

Signed and Sealed this

Thirtieth Day of August, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,716,176
DATED : December 29, 1987
INVENTOR(S) : Christa Fest, et al.

It is certified that error appears in the above-identified patent and that said Letters Patent is hereby corrected as shown below:

Col. 2, line 15             After "formula (III)" insert --R-NCO--

Signed and Sealed this

Eighth Day of November, 1988

Attest:

DONALD J. QUIGG

Attesting Officer      Commissioner of Patents and Trademarks